United States Patent [19]

Ifuku

[11] Patent Number: 5,377,253
[45] Date of Patent: Dec. 27, 1994

[54] X-RAY DIAGNOSTIC APPARATUS
[75] Inventor: Akira Ifuku, Ootawara, Japan
[73] Assignee: Kabushiki Kaisha Toshiba, Kawasaki, Japan
[21] Appl. No.: 68,161
[22] Filed: May 28, 1993
[30] Foreign Application Priority Data
  May 29, 1992 [JP] Japan .................. 4-139233
[51] Int. Cl.⁵ ................................. A61B 6/14
[52] U.S. Cl. ...................... 378/162; 378/176; 378/98.2
[58] Field of Search ............... 378/162, 176, 183, 190, 378/204, 98, 99, 4, 98.5; 358/111

[56] References Cited
U.S. PATENT DOCUMENTS

| | | | |
|---|---|---|---|
| 4,739,480 | 4/1988 | Oono et al. | 378/166 |
| 5,179,579 | 1/1993 | Dove et al. | 378/99 |
| 5,195,123 | 3/1993 | Clement | 378/162 |

Primary Examiner—David P. Porta
Assistant Examiner—Don Wong
Attorney, Agent, or Firm—Oblon, Spivak, McClelland, Maier & Neustadt

[57] ABSTRACT

An X-ray diagnostic apparatus for diagnosing an object to be examined, includes X-ray radiating means for radiating an X-ray on the object to be examined, means for detecting the X-ray passed through the object to be examined and obtaining an X-ray static image of the object to be examined, and means for adding discrimination information to the X-ray static image of the object to be examined and outputting a static image to which discrimination information is added. In addition, the X-ray diagnostic apparatus of the present invention further comprises means for recording a motion image of the object having information corresponding to the static image having to which the discrimination information has been added.

9 Claims, 4 Drawing Sheets

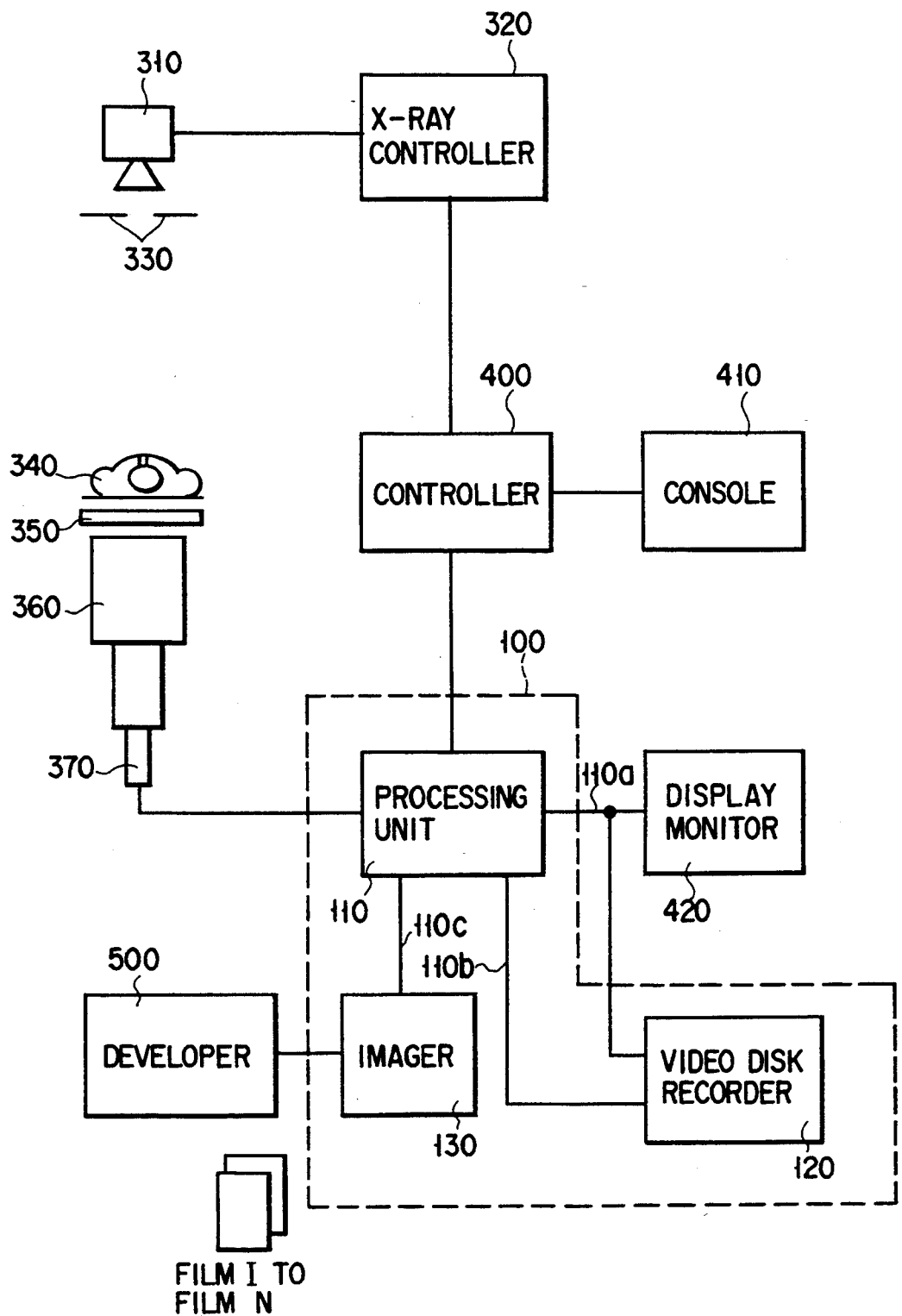
F I G. 2

| PATIENT ID NO. | START TIME | STOP TIME | FRAME NO. WHEN X-RAY :ON | FRAME NO. WHEN X-RAY :OFF | DIVISION |
|---|---|---|---|---|---|
| 1234 | 14:00 | 14:12 | 1200 | 1360 | FLUOROSCPIC IMAGE |
| 〃 | 14:13 | 14:13 | 1361 | 1361 | X-RAY IMAGE |
| ---- | | | | | |

F I G. 5

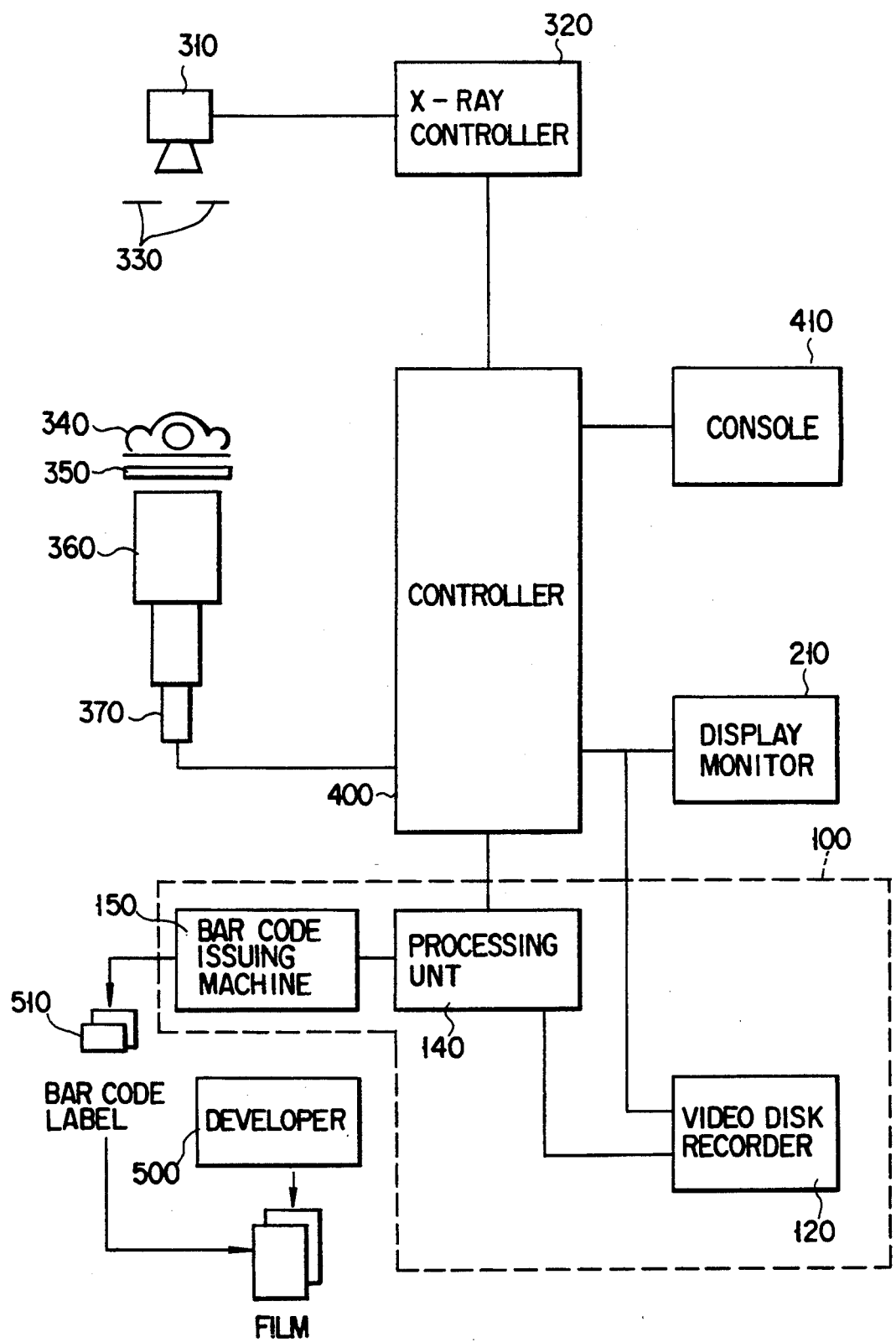
F I G. 6

Х-RAY DIAGNOSTIC APPARATUS

BACKGROUND OF THE INVENTION

1. Field of the Invention

The present invention relates to an X-ray diagnostic apparatus in which a desired motion image corresponding to a static image can be easily obtained in an X-ray diagnosis, particularly, fluoroscopic or X-ray imaging, thereby improving accuracy of diagnosis.

2. Description of the Related Art

In a conventional X-ray diagnosis, a method is mainly used in which a doctor inspects an image (static image) obtained by X-ray film imaging. Also, a motion image (hereinafter called as "fluoroscopic image") using an image intensifier-TV system is inspected in addition to the inspection of the static image as required. Generally, since the X-ray image is obtained by radiating an X-ray having high energy on an object to be examined for a short period of time, an image having high contrast can be obtained. On the other hand, since such a three-dimensional object to be examined is expressed by a two-dimensional image, there is a drawback in that the depth of the object cannot be easily examined. In the fluoroscopic image, since it is required that the X-ray be radiated on the object to be examined for a long period of time, energy of the X-ray must be low. Due to this, the obtained image has a large amount of noise with low contrast. On the other hand, in the fluoroscopic image, there is an advantage that the depth of the three-dimensional object can be easily examined.

In recent years, there has been studied an imaging method using no X-ray film, for example, a method (digital imaging) in which an X-ray having high energy is radiated on the object to be examined for a short period of time and the object is imaged as an electrical signal by use of a solid imaging device such as a CCD. Then, there has been used a diagnostic method in which the fluoroscopic image or the X-ray image is recorded in a recording medium, which is on the market, such as a video tape recorder (VTR) or a video disk recorder, and the image is reproduced for diagnosis. However, the doctor can neither easily retrieve a desired image nor reproduce the image.

As mentioned above, in the prior art, there is difficulty in judging abnormality. Moreover, in the diagnostic method, which has come into wide use recently, the doctor cannot easily reproduce a desired image.

SUMMARY OF THE INVENTION

In consideration of the above-mentioned problem, the present invention has been made, and an object of the present invention is to provide an X-ray diagnostic apparatus wherein a doctor can easily observe a desired image.

According to the present invention, there is provided an X-ray diagnostic apparatus for diagnosing an object to be examined, comprising X-ray radiating means for radiating an X-ray on the object to be examined, means for detecting the X-ray passed through the object to be examined and obtaining an X-ray static image of the object to be examined, and means for adding discrimination information to the X-ray static image of the object to be examined and outputting a static image to which discrimination information is added. In addition, the X-ray diagnostic apparatus of the present invention further comprises means for recording a motion image of the object having information corresponding to the static image having discrimination information.

According to the present invention, since an unclear portion on the static image can be observed by the motion image corresponding to the static image, it is unnecessary to perform the imaging operation again due to the difference in timing. Therefore, examining time can be shortened, and the amount of X-ray radiation can be reduced. Moreover, according to the present invention, since the observation can be easily performed by not only the static image but also the motion image, diagnostic data of the object to be examined can be increased, and accuracy of diagnosis can be improved.

Furthermore, according to the present invention, an operator does not have to be careful about timing, which is taken in a case that a portion where the object to be examined is moving, for example, a gullet is imaged. Therefore, stress on the operator can be reduced.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 2 is a block diagram showing the details of recording means 100 of FIG. 1;

FIG. 5 is a view showing an example of a data array recorded in a video disk; and FIG. 6 is a block diagram showing the detail of recording means 100 according to a second embodiment of the present invention.

DETAILED DESCRIPTION OF THE PREFERRED EMBODIMENTS

An X-ray diagnostic apparatus according to an embodiment of the present invention will be explained with reference to the drawings.

Figure 1:
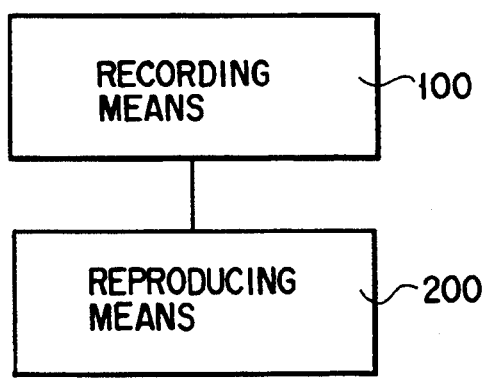
FIG. 1 is a block diagram showing a schematic structure of an X-ray diagnostic apparatus according to a first embodiment of the present invention.

FIG. 1 is a block diagram showing a schematic structure of the X-ray diagnostic apparatus according to the first embodiment of the present invention.

The X-ray diagnostic apparatus of the present invention basically comprises recording means 100 for recording a static image and a motion image to correspond to each other, and reproducing means 200 for reproducing a corresponding motion image based on data recorded in the static image.

Figure 3:
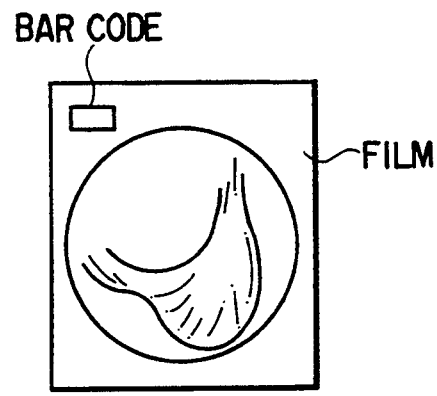
FIG. 3 is a view showing an example of a film obtained by recording means 100 of FIG. 1.
Figure 4:
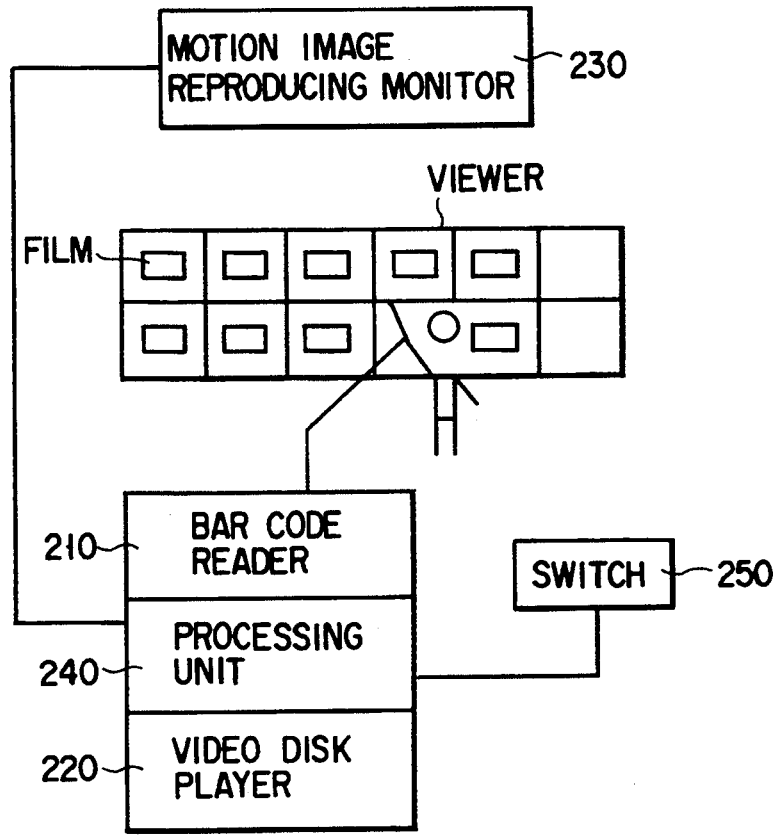
FIG. 4 is a block diagram showing reproducing means 200 of FIG. 1.

FIGS. 2 and 4 are block diagrams showing the details of recording means 100 and reproducing means 200 of FIG. 1, respectively. FIG. 3 is a view showing an example of a film (static image) obtained by recording means 100. FIG. 5 is a view showing an example of a data array recorded in a motion image recording medium, for example, a video disk. FIGS. 2 to 5 will explain the details of the X-ray diagnostic apparatus according to the first embodiment of the present invention.

The following will explain a method for recording the static image and the motion image to correspond to each other with reference to FIGS. 2 and 5.

An X-ray tube 310 radiates an X-ray based on a signal sent from an X-ray controller 320. A radiation area of the X-ray is controlled by a collimator 330, and the X-ray is radiated on an object 340 to be examined. The X-ray, which has passed through the object 340, passes through a spot shot unit 350, and enters an image intensifier 360 (hereinafter called as "I.I."). The X-ray entered I.I. 360 is converted to an optical image and amplified by I.I. 360. Thereafter, the optical image is inputted to a camera 370 through an optical system (not shown). An optical signal, which is converted to an image signal, is converted to a digital signal by an analog/digital (A/D) converter (not shown) and inputted to a processing unit 110.

The digital signal inputted to the processor 110 outputs three signals, that is, an image signal 110a, a video disk recorder control signal 110b, and a control signal 110c based on a signal, which is inputted from a console 410 through a controller 400.

The image signal 110a is converted to an analog signal by a digital/analog converter (not shown), and inputted to a display monitor 420 and a video disk recorder 120.

The video disk recorder control signal 110b to be explained later is inputted to the video disk recorder 120.

The control signal 110c is inputted to an imager 130, and a process to be explained later is performed by the imager 130, and films 1 to N are developed by a developer 500.

An operation of the above-structured X-ray diagnostic apparatus of the present invention will be explained.

If a doctor or an operator sets fluoroscopic and X-ray imaging conditions (hereinafter called "radiation condition") such as energy of the X-ray (voltage applied to the X-ray tube), radiation time, etc. by the console 410, data relating to the radiation conditions is transmitted to the X-ray controller 320 through the controller 400.

If fluoroscopy is started, a fluoroscopic start signal is inputted to the X-ray controller 320 through the controller 400. At the same time, the fluoroscopic start signal is inputted to the processing unit 100.

By the fluoroscopic start signal inputted to the X-ray controller 320, the X-ray controller 320 applies high voltage to the X-ray tube 310 based on the predetermined radiation conditions of the X-ray. The X-ray tube 310 generates an X-ray having predetermined energy based on the high voltage applied from the X-ray controller 320, and radiates the object to be examined. In this case, the radiation area of the X-ray is controlled by the collimator 330 in order to obtain a desired radiation area.

The X-ray, which has passed through the object 340, enters I.I. 360. The X-ray entered I.I. 360 is converted to an optical image and amplified by I.I. 360. Thereafter, the amplified optical image is inputted to the camera 370 through an optical system (not shown). An image signal is converted to a digital signal by an analog/digital converter (not shown) and inputted to the processing unit 110. The image signal inputted to the processing unit 110 is converted to an analog signal by a digital/analog converter (not shown), and outputted to the display monitor 420. The display monitor 420 directly displays the image signal, which is inputted to the display monitor 420 from the processing unit 110 through the digital/analog converter.

A fluoroscopic start signal other than the image signal, which is inputted from the processing unit 110, is inputted to the video disk recorder 120. By the fluoroscopic start signal, the video disk recorder 120, which can provide a random access, starts recording a fluoroscopic image. The recording operation is continued until a fluoroscopic end signal is inputted to the video disk recorder 120. Separated from image data, data of image management is recorded on a video disk. as shown in FIG. 5. That is, In FIG. 5, it is shown that fluoroscopic images of patient ID No. 1234 is collected from 14:00 until 14:12, and recorded in frames Nos. 1200 to 1360. By this operation, first fluoroscopic image data is recorded on the video disk recorder 120.

In a case where the start of imaging is instructed by the console 410, similar to the case of the fluoroscopic imaging, an imaging start signal is outputted to the X-ray controller 320 and the processing unit 110 through the controller 400. In this case, a film is mounted on the spot shot unit 350 as required, thereby a film imaging is performed.

Similar to the case of the fluoroscopic imaging, an X-ray, which is generated from the x-ray tube based on the imaging start signal sent from the console 410, passes through the object 340. Thereafter, the X-ray is converted to an optical image by I.I. 360, and changed to an image signal by the camera 370. Thereafter, the image signal is analog/digital-converted (not shown), and inputted to the processing unit 110. The image signal inputted to the processing unit 110 is inputted to the display monitor 420 and the video disk recorder 120 similar to the case of the fluoroscopic imaging. The display monitor 420 displays the inputted image as it is. The video disk recorder 120 records the input image, and image management data as shown in FIG. 5 in accordance with the image start signal inputted through the processing 110 and the image end signal. In this embodiment, as shown in FIG. 5, the X-ray imaging, which corresponds to data of the fluoroscopic image recorded in frame No. 1200 to frame No. 1360, starts and ends at 14:13, and the X-ray image is recorded in frame No. 1361 (in this embodiment, only one frame (one image) is used, but a plurality of frames can be used as required).

The processing unit 110 outputs the image start signal to the video disk recorder 120. Other than this operation, the processing unit 110 prepares a bar code image including a frame number added to the previous video disk, and outputs the image to the imager 130. The imager 130 prints the bar code and the image in a film (not shown). The film is developed by a developer 500, thereby a desired film can be obtained. FIG. 3 shows one example of the film (static image) obtained by recording means 100.

With reference to FIG. 2, there will be explained a method for obtaining a corresponding motion image recorded in the film to the video disk by use of the above-obtained film and the video disk.

The reproducing device 200 shown in FIG. 4 comprises a bar code reader 210 reading the bar code recorded in the film, a video disk player 220 for reproducing the video disk, a motion image reproducing monitor 230, and a processing unit 240 performing the control of various portions.

An operation of the above-structured reproducing device will be explained.

A doctor arranges the film obtained by the recording device 100 on an X-ray photograph reader, and diagnoses. In a case where abnormality is detected on the film or the doctor wishes to know more specific examination result, the diagnosis is made by use of the motion image, so that more specific data can be obtained.

The motion image recorded in the video disk by the bar code added to the film is retrieved and observed to perform more specific diagnosis. A method for reproducing the motion image will be explained.

when the doctor wishes to have specific data of a desired film, the bar code added to the film by the recording device 100 is read by the bar code reader 210. Data read by the bar code reader 210 is outputted to the processing unit 240. The processing unit 240 outputs to the video disk player 220. The video disk player 220 retrieves the position of the motion image on the video disk corresponding to the bar code read based on data. Then, the desired motion image corresponding to the film through the processing unit 240 is instantaneously outputted to the motion image reproducing monitor 230. For example, in FIG. 5, if the bar code added to the imaging film is read by the bar code reader 210, the video disk player 220 retrieves start frame No. 1200 of fluoroscopic image data corresponding to the frame No. 1361 of the X-ray image on the disk, and outputs fluoroscopic image data of frames Nos. 1200 to 1360 to the motion image reproducing monitor 230.

In this case, prior to the reproduction of fluoroscopic image data, the X-ray image of the frame No. 1361 may be displayed for confirmation.

By the above-explained operation, the desired motion image corresponding to the film can be easily retrieved.

In a case where the desired motion image is reproduced and diagnosis using the desired motion image is ended, and fluoroscopy is started again, the following operations are performed.

If the fluoroscopic start signal is inputted to the video disk recorder 120 through the controller 400 and the processing unit 110 from the console 410, the video disk is advanced to a frame (frame No. 1362 not shown in FIG. 5) next to the final frame shown in FIG. 5. The following operation is the same as the cases of the normal fluoroscopy and X-ray imaging. Therefore, fluoroscopy and X-ray imaging can be newly performed without destroying data erroneously recorded.

The reproducing device of FIG. 4 further comprises a switch 250 in order to perform the examination easily and surely by use of the motion image. The switch 250 has the following functions.

That is, the switch 250 controls the frame-by-frame feeding of the reproduced image in which each motion image is observed as a static image every unit time. Moreover, the switch 250 controls a slow reproduction in which a reproduction speed is made late to perform more specific observation or controls a repeat reproduction in which the observation of the corresponding portion is repeatedly performed.

As mentioned above, according to the present invention, since the static image and the motion image are linked, the motion image corresponding to the static image can be easily obtained. Therefore, the conventional observation, which is two-dimensionally carried out, can be displayed by the motion image, so that the image can be treated as a three-dimensional image. Moreover, regarding whether or not a portion difficult to be discriminated is abnormal, since such a portion can be confirmed by the motion image, the discrimination whether it is normal or abnormal can be easily performed. Furthermore, even in a case where the present invention is applied to the conventional diagnosis using the video disk, since a desired motion image can be instantaneously obtained, the diagnosis can be easily and rapidly performed.

The above first embodiment showed the example using a structure which is different from the structure of the conventional X-ray diagnostic apparatus. However, the present invention may be directly applied to the conventional X-ray diagnostic apparatus.

FIG. 6 is a view showing the schematic structure of a second embodiment in which the present invention is directly applied to the conventional X-ray diagnostic apparatus. A portion where a motion image corresponding to a recorded static image is retrieved and displayed is omitted since it is the same as in the first embodiment. The second embodiment shows only a portion where the static image and the motion image are made to correspond to each other and recorded. The same reference numerals are added to portions corresponding to the first embodiment, and the specific explanation is omitted.

Similar to the conventional X-ray diagnostic apparatus, the X-ray diagnostic apparatus according to the second embodiment of FIG. 6 comprises X ray controller 320, console 410, controller 400, X-ray tube 310, collimator 330, spot shot unit 350, I.I. 360, camera 370, and display monitor 420. In addition to these apparatuses, the X-ray diagnostic apparatus according to the second embodiment comprises a video disk recorder 120, a processing unit 140, and a bar code issuing machine 150.

An operation of the above-structured apparatus will be explained.

If a doctor or an operator sets the radiation condition by the console 410, data relating to the radiation conditions is transmitted to the x-ray controller 320 through the controller 400.

If fluoroscopy is started, the fluoroscopic start signal is inputted to the X-ray controller 320 through the controller 400. At the same time, the fluoroscopic start signal is inputted to the processing unit 140.

When the fluoroscopic start signal is inputted to the X-ray controller 320, the X-ray controller 320 applies high voltage to the X-ray tube 310 based on the predetermined radiation conditions of the X-ray. The X-ray tube 310 generates an X-ray having predetermined energy based on the high voltage applied from the X-ray controller 320, and radiates the object 340 to be examined. In this case, the radiation area of the X-ray is controlled by the collimator 330 in order to obtain a predetermined radiation area.

The X-ray, which has passed through the object 340, enters I.I. 360 through the spot shot unit 350. The X-ray entered I.I. 360 is converted to an optical image and amplified by I.I. 360. Thereafter, the amplified optical image is inputted to the camera 370 through an optical system (not shown). An image signal is converted to a digital signal by an analog/digital converter (not shown) and inputted to the processing unit 140. The image signal inputted to the processing unit 140 is converted to an analog signal by a digital/analog converter (not shown), and outputted to the display monitor 420. The display monitor 420 directly displays the image signal, which is inputted to the display monitor 420 from the processing unit 140 through the digital/analog converter.

A fluoroscopic start signal other than the image signal, which is inputted from the processing unit 140, is inputted to the video disk recorder 120. By the fluoroscopic start signal, the video disk recorder 120, which can provide a random access, starts recording a fluoroscopic image. The recording operation is continued till a fluoroscopic end signal is inputted to the video disk recorder 120. Separated from image data, data of image management is recorded in the video disk as shown in FIG. 5. In this embodiment, it is shown that fluoroscopic images of patient ID Nos. 1234 to 1238 are collected from 14:00 until 14:12, and recorded in frames Nos. 1200 to 1360. By this operation, first fluoroscopic image data is recorded on the disk.

In a case where the start of imaging is instructed by the console 410, similar to the case of the fluoroscopic imaging, an imaging start signal is outputted to the X-ray controller 320 and the processing unit 140 through the controller 400. In this case, a film is mounted on the spot shot unit 350, and a necessary static image is formed.

Similar to the case of the fluoroscopic imaging, an X-ray, which is generated from the X-ray tube based on the imaging start signal sent from the console 410, passes through the object 340. Thereafter, the X-ray is converted to an optical image by I.I. 360, and changed to an image signal by the camera 370. Thereafter, the image signal is analog/digital-converted (not shown), and inputted to the processing unit 140. The image signal inputted to the processing unit 140 is inputted to the display monitor 420 and the video disk recorder 120, similar to the case of the fluoroscopic imaging. The display monitor 420 displays the inputted image as it is. The video disk recorder 120 records the input image, and image management data as shown in FIG. 5 in accordance with the image start signal inputted through the processing 140 and the image end signal. In this embodiment, as shown in FIG. 5, the X-ray imaging, which corresponds to data of the fluoroscopic image recorded in frame No. 1200 to frame No. 1360, starts and ends at 14:13, and the X-ray image is recorded in frame No. 1361 (in this embodiment, only one frame (one image) is used, but a plurality of frames can be used as required).

The processing unit 140 outputs the image start signal to the video disk recorder 120. Other than this operation, the processing unit 140 prepares a bar code image including a frame number added to the previous video disk, and outputs the image to the bar code issuing machine 150. The bar code issuing machine 150 issues a bar code label 510 based on the bar code.

A film is provided in the spot shot unit 350, and the object 340 is imaged in the film. The film is developed by the developer 500, and the issued bar code label 510 is adhered thereto.

By the above operation, similar to the first embodiment, the film in which the motion image can be easily retrieved, can be formed, and the motion image corresponding to the film is recorded in the video disk. The explanation of the reproducing operation will be omitted since it is the same as the first embodiment.

Therefore, the same technical advantage as the first embodiment can be obtained.

The present invention is not limited to the above-explained embodiments.

According to the above-explained embodiments, the motion image was reproduced by the bar code as a discrimination code. However, any code may be used if the film is made to correspond to the motion image and the apparatus can read the code. Moreover, a character and a number, which the operator can read, are printed in the film, and the motion image may be reproduced by the operator's input of the character and number.

The above embodiments explained the case in which the bar code is added to each film and the motion image is retrieved as observing the film. In the case that a list is printed, the output is performed in the form that the bar code is added to the list, and the bar code is read from the list, thereby a desired motion image can be obtained.

In the above embodiments, the static image was explained as a film. However, the static image is not limited to the film. For example, a discrimination code may be added to the static image such that the static image on CRT is stored in a memory. The static image may be outputted into the film if necessary.

Furthermore, the recording medium for the motion image is not limited to the video disk, and VTR and the other recording medium.

It is true of course that the present invention can be variously modified without deviating from the scope of the present invention.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An X-ray diagnostic apparatus for diagnosing an object to be examined, comprising:
   X-ray radiating means for radiating X-rays on said object to be examined;
   means for detecting X-rays that have passed through said object to be examined and obtaining an X-ray static image of said object to be examined;
   means for adding discrimination information to said X-ray static image of said object to be examined and outputting a static image to which said discrimination information is added; and
   motion image recording means for recording a motion image of said object to be examined, said motion image having information corresponding to said static image to which said discrimination information has been added.

2. An X-ray diagnostic apparatus according to claim 1, wherein said means for adding discrimination information comprises an X-ray photographic apparatus for imaging said X-ray static image on a film.

3. An X-ray diagnostic apparatus according to claim 1, wherein said means for adding discrimination information comprises a display monitor for displaying said X-ray static image.

4. An X-ray diagnostic apparatus according to claim 1, wherein said motion image recording means includes means for recording a new motion image immediately following the latest-recorded image.

5. An X-ray diagnostic apparatus according to claim 1, wherein said motion image recording means records a recording position of said motion image in addition to said motion image to which said discrimination information is added.

6. An X-ray diagnostic apparatus according to claim 1, wherein said motion image recording means records said motion image in accordance with an on/off state of said X-rays radiated from said X-ray radiating means.

7. An X-ray diagnostic apparatus according to claim 1, wherein said discrimination information added to said static image is comprised of a bar code.

8. An X-ray diagnostic apparatus according to claim 1, further comprising means for reproducing said motion image recorded by said motion image recording means.

9. An X-ray diagnostic apparatus according to claim 8, wherein said means for reproducing said motion image includes means for controlling frame-by-frame feeding of a reproduced image, repeat reproduction, and slow reproduction at the time of reproducing a desired motion image.

* * * * *